United States Patent [19]

Brockway et al.

[11] Patent Number: 5,356,878

[45] Date of Patent: Oct. 18, 1994

[54] GEL FILTRATION OF FACTOR VIII

[75] Inventors: William J. Brockway, Oakland; Richard L. Seng, Guerneville, both of Calif.

[73] Assignee: Miles Inc., Berkeley, Calif.

[21] Appl. No.: 852

[22] Filed: Jan. 4, 1993

Related U.S. Application Data

[60] Division of Ser. No. 587,815, Sep. 24, 1990, Pat. No. 5,177,591, which is a continuation of Ser. No. 135,966, Dec. 21, 1987, abandoned.

[51] Int. Cl.$^5$ .................. A61K 35/14; C07K 13/00; C07K 3/20
[52] U.S. Cl. ................................ 514/21; 530/383; 424/530
[58] Field of Search .................. 530/383; 424/86, 87, 424/530; 514/21

[56] References Cited

U.S. PATENT DOCUMENTS

| 4,020,713 | 5/1977 | Bick et al. | 530/383 |
| 4,670,543 | 6/1987 | Bourgois et al. | 530/383 |
| 4,774,323 | 9/1988 | Newman et al. | 530/383 |

OTHER PUBLICATIONS

Thorell et al. "An In Vivo Study of a New Factor VIII Layer Purity Preparation", Thromb. Res vol. 31, pp. 375-385 (1983).

Primary Examiner—Howard E. Schain
Assistant Examiner—P. Lynn Touzeau
Attorney, Agent, or Firm—James A. Giblin; Bertram Bradley

[57] ABSTRACT

Highly purified antihemophilic factor is produced by a process comprising a PEG precipitation step, a gel filtration step and a virus inactivation step. Al(OH)$_3$ adsorption and PEG precipitation carried out at room temperature allow processing to proceed directly to a gel filtration step.

3 Claims, No Drawings

GEL FILTRATION OF FACTOR VIII

This application is a division of application Ser. No. 07/587,815, filed Sep. 24, 1990, now U.S. Pat. No. 5,177,591, which is a continuation of 07/135,966, filed Dec. 21, 1987, now abandoned.

BACKGROUND OF THE INVENTION

1. Field of the Invention

The present invention relates to methods of preparing antihemophilic factor (AHF) from human plasma. AHF is now known to consist of several components, the component which is active in treating hemophilia A being Factor VIII:C.

2. Description of the Prior Art

Numerous patents and publications exist which relate to the preparation of AHF concentrates as part of the fractionation of human plasma. Such processes have been in commercial use for approximately 20 years, and numerous processing variations have been described, the vast majority of which are directed to the inherent problems in such processes, namely virus safety, yield, and specific activity of the resultant concentrate. Specific activity refers to the activity of the Factor VIII, expressed in international units, according to a currently accepted standard, per mg of total protein.

Although gel filtration or chromatography, except for affinity chromatography such as described in Zimmerman et al, U.S. Pat. No. Re. 32,011 (U.S. Pat. No. 4,361,509) is not, to the inventors' knowledge, in current commercial use, several chromatography processes have been described. It is important to note that all affinity chromatography or rDNA processes will result in AHF having detectable amounts of non-human protein.

For example, PCT Application Publication No. WO 86,04486 discloses a method for purifying AHF by "hydration additives", i.e. using column chromatography in the presence of sugars, polyols, amino acids or salts. The low yield of prior art chromatography processes is described.

The hydration additives serve to stabilize the AHF. Cryoprecipitate is dissolved in a buffer, aluminum hydroxide may be added and the supernatant collected. A PEG precipitation step is carried out. One or two column chromatography steps are then carried out, using resins such as QAE Sephadex A-25, QAE-Sepharose 4B or aminohexyl (A-H) Sepharose. The first chromatography step is based on anion exchange, the second on hydrophobic affinity.

Andersson, EP 197901, discloses a method for preparing fragments of AHF using immunoaffinity chromatography followed by HPLC on an anion-exchange adsorbent. The anion exchange adsorbent may be Mono Q gel or TSK DEAE 5 PW gel. Fragments are then obtained by incubation with thrombin.

Johnson, U.S. Pat. No. 4,397,841, discloses preparation of Factor VIII:C by fractionation of plasma with a sequence of adsorption steps employing polyelectrolyte copolymers in the presence of heparin. A suitable resin is a copolymer of ethylene and maleic anhydride.

Chavin et al, U.S. Pat. No. 4,495,175, disclose the preparation of highly purified AHF from AHF concentrate. The concentrate is subjected to a separation on the basis of Stokes' radius, which may be accomplished, for example, by gel permeation chromatography on cross-linked agarose (such as BioGel A-15M or Sepharose CL-4B). The pool is then concentrated by precipitation or diafiltration; calcium or magnesium cations are added to reduce the Stokes' radius, and a separation on the basis of Stokes' radius is again carried out.

Various other steps such as are employed in the present process have been disclosed in the prior art. However, as described below, novel and unexpected results and modifications are embraced by the present invention.

Liu et al, U.S. Pat. No. 4,170,639, for example, disclose a process for preparing AHF comprising the steps of subjecting resolubilized cryoprecipitate to aluminum hydroxide adsorption at an acid pH and 4° C.; filtration; and, optionally, ultrafiltration.

Rasmussen et al, U.S. Pat. No. 4,650,858, disclose a process for producing AHF using a 4% PEG precipitation step at 18°–22° C. to remove fibrinogen. This is followed by a second PEG precipitation step at 18°–22° C. with 12% PEG in the presence of an amino acid such as 2M glycine to precipitate the AHF.

Shanbrom, U.S. Pat. No. 4,069,216, discusses PEG precipitation as disclosed in the prior art, e.g. his U.S. Pat. No. 3,631,018 wherein room temperature precipitation necessitates a subsequent washing and/or glycine or alcohol precipitation step, since the PEG is used in high concentrations (10–12%). Cold precipitation using lower concentrations of PEG (2½%) resulted in a less purified product.

Liautaud et al, U.S. Pat. No. 4,387,092, disclose an improvement to Shanbrom U.S. Pat. No. 4,069,216 in that the fibrinogen precipitation step is carried out at below 15° C. with less than 4% polyol.

Rolson, U.S. Pat. No. 3,415,804, discloses plasma fractionation with PEG at room temperature, around 20° C. At 0–4% PEG, fibrinogen precipitated, gamma globulin precipitated at 4–8%, beta globulin at 8–12% and alpha-1 and alpha-2 globulins and albumins at greater than 12% PEG.

Finally, relevant prior art exists with regard to virus inactivation of AHF concentrates.

Neurath et al, U.S. Pat. No. 4,540,573, disclose viral inactivation of Factor VIII preparations through the use of tri-(n-butyl) phosphate (TNBP). It is there suggested that TNBP may be added to the plasma pool, and AHF can be separated from TNBP by a precipitation step, such as with glycine. In the Examples, TNBP is added to AHF solutions having 8–10 u/mL F.VIII activity.

Andersson et al, U.S. Pat. No. 4,168,300, disclose a method of removing hepatitis virus from plasma by adsorbing the HBsAg, or Av-antigen onto a beaded agarose gel, or a copolymer gel, having a hydrophobic ligand coupled thereto.

Lembach, U.S. Pat. No. 4,534,972, discloses the use of copper phenanthroline for viral inactivation of AHF preparations. The substance is added after fractionation and may be removed by diafiltration.

SUMMARY OF THE INVENTION

High yields of antihemophilic factor (AHF) can be achieved using milder processing steps in combination with a chemical viral inactivation process and gel filtration step to provide highly purified AHF which is substantially free from infectious agents, without substantial loss of therapeutic or immunological activity.

Recent developments have provided improved processes for rendering plasma proteins substantially free from infectious agents. For example see U.S. Pat. No.

4,534,972 disclosing the use, for example, of copper phenanthroline. Tri-N-butyl phosphate (TNBP) may also be used as a chemical, as opposed to heat, viral inactivation step.

In one particular aspect of the present invention, cryoprecipitate is recovered by centrifugation from thawed pools of fresh frozen human plasma. Extraneous non-AHF proteins are removed by acid precipitation and adsorption with Al(OH)$_3$ and PEG precipitation under conditions which produce high precipitation of non-AHF proteins. As a result, a chill step is not needed. The AHF is then precipitated with glycine and sodium chloride. Solubilized AHF concentrate is then treated for viral inactivation and then gel-filtered. The preferable gel has a 5 million dalton cut-off and 100–200 mesh; it serves to separate AHF from the viral inactivation compound(s) as well as to separate the AHF from other plasma components.

AHF is then lyophilized after sterile filtration in the presence of albumin. The AHF produced by this process is free of non-human proteins such as would be found in a monoclonal-purified product, is of high specific activity, and has desirable amounts of von Willebrand Factor.

DETAILED DESCRIPTION OF THE PREFERRED EMBODIMENTS

Example 1

Cryoprecipitate (cryo) from a normal plasma pool of plasmapherised donors was dissolved by adding 3 Kg of WFI/Kg cryo. The WFI can include up to 60 u/ml of sodium heparin before the cryo is added. 30.2 Kg of cryo was added to 90.5 Kg WFI at a temperature of 27° C. and mixed to dissolve the cryo. The temperature range of WFI is preferably 17°–37° C., most preferably 24°–30° C. Although the ratio of 1 part cryo/3 parts WFI are used in the example, 1 part cryo/4 parts WFI can be used to obtain the same results.

The cryo/WFI mixture was stirred for 30 minutes until dissolved. The resulting temperature was 21° C., a preferable range being 18°–25° C. The $A_{280}$ was 41.2, a preferable range being 38 to 44 and a pH of 7.75, preferable range being 7.6–8.0.

The pH of the dissolved cryo/WFI solution was adjusted to 7.0, the preferable range being 6.0–8.0, most preferably 6.8–7.2 with the dropwise addition of 270 ml of 1N acetic acid and the suspension was stirred for 15 minutes. The average yield was 116% with a yield range of 110–127%. The apparent yield increase is due to removal of fibrinogen and other components which interfere in the AHF assay. The foregoing steps may be carried out at room temperature to avoid a chill step and additional precipitation, and to avoid protein denaturation.

For the adsorption step, 4826 ml of aluminum hydroxide, Al(OH)$_3$, gel was added to the acid cryosuspension and stirred for 10 minutes to bind the vitamin K dependent factors. The amount of Al(OH)$_3$ gel represents 160 ml of Al(OH)$_3$ gel per Kg of starting cryo, a preferable range being 100–250 ml of Al(OH)$_3$ gel per Kg of cryo. The average yield across this step is 94% with a yield range of 90–100%.

For polyethylene glycol (PEG) precipitation, 3.6 Kg of PEG 3350 (3% PEG) was added to the Al(OH)$_3$ - acid cryo suspension and the pH was readjusted to 7.06 with 16 ml of 1M acetic acid. The pH range being 6.0–8.0, more preferably 6.8–7.3. The concentration of PEG can range from 2.5–5%. The suspension was stirred for 23 minutes before centrifugation. The temperature of the suspension was 21.5° C., preferably not less than 10° C.

The suspension was centrifuged using a Westphalia BKA-6 centrifuge at 4 l/min flow rate, the preferable range being 2–6 l/min. The effluent temperature was maintained at 20° C., the preferable range being 18°–25° C. with the influent temperature of 21.5° C., the preferable range being 20°–25° C.

The resulting precipitate was harvested, weighed and discarded. The 10.7 Kg precipitate represented 35.4% of the starting cryo. The average precipitate being 32.4% with a range of 29.0–36.3%.

The PEG effluent weighed 116.6 Kg, had an $A_{280}$ of 10.4, pH 7.26 at a temperature of 20° C. The temperature range is preferably 20°–23° C., if necessary a warming step can be added for a PEG effluent having a temperature lower than 20° C. The average yield of AHF recovered through the PEG step was 78% with a range of 74.3–86.1.

An important advantage is recognized in the elimination of the chill step conventionally used in the PEG precipitation. This is an advantage because a chill step will precipitate fibrinogen, fibronectin, etc., but also will precipitate AHF, reducing yield.

To the PEG effluent was added 15.2 Kg of solid L-glycine (or 13% glycine) while maintaining the pH at 7.0, preferable range 6.0–8.0, by the addition of 200 ml of 1M sodium hydroxide. The addition of glycine lowered the temperature of the PEG effluent to about 15° C. The solution was warmed to 20° C., the preferable range being 20°–23° C. The solution was stirred for 20 minutes until dissolved.

To the glycine-PEG effluent solution was added 16.3 Kg solid NaCl (or 14% NaCl) while maintaining the pH at 7.0, the preferable range being 6.0–8.0, with 200 ml of 1M NaOH. The final temperature was adjusted to 20° C. the preferable being 20°–23° C. The final pH was 7.03 with a range of 6.9–7.2. The solution was stirred for 25 minutes until dissolved.

The glycine-NaCl - PEG effluent was centrifuged to remove the AHF paste at the flow rate of 2.0 l/min. The inlet temperature was 20° C., the preferable range being 20°–23° C. The effluent temperature was maintained at 21°–22° C., the preferable range being 18°–25° C. The $A_{280}$ of the effluent was measured at 9.1 and the effluent discarded.

The resulting final AHF paste obtained is a very good working paste weight to avoid loss of AHF or high volume of column gel. Too low a paste weight results in loss of AHF, too high a paste weight requires a large volume of column gel for the gel filtration step.

The harvested AHF paste weighed 1.03 Kg. It was dissolved in a buffer containing 0.02M L-histidine, 0.10M ammonium formate, 1.5% mannitol, 0.001M CaCl$_2$ at a pH of 7.0, the preferable range being 6.9–7.1. The buffer can contain not more than 0.2M ammonium formate, 0.06M L-histidine, 0.003M CaCl$_2$ and 3% mannitol. The buffer should minimize the protein modification, i.e., non-specific binding of copper phenanthroline. Alternative buffers can be used, for example: Water for Injection (WFI); 0.15M NaCl, 0.001M, CaCl$_2$, pH 7.2; 0.05M imidazole, pH 7.0; or 0.05M Tris HCl/0.15M NaCl, pH 7.0, or 0.02M L-histidine, 0.15M NaCl, 0.001M CaCl$_2$, pH 7.2.

The resulting dissolved AHF concentrate had an $A_{280}$ of 33.2, a weight of 3.84 Kg and a potency of 432 u/ml. In previous runs the average potency was 232 u/ml, the range was 130–287.5 u/ml. Because of this much higher than normal potency as compared to previous PEG precipitation methods, the chemical treatment for vital inactivation and gel filtration steps are performed without the necessity of a further concentration step, as previously required, such as ultrafiltration. The recovery of units of AHF as compared to the dissolved cryo was 63.2%, the average 67.3% with the range being 56.7°–71.8° C. In previous runs, the yield of AHF from the PEG effluent to the dissolved AHF concentrate was an average of 78.3% with the recovery range being 68.3–90.0%.

The solubilized AHF can be frozen at −20° C. or colder and stored at −70° C. or processed immediately.

The frozen (−70°) AHF concentrate was thawed in a 27° C. water bath for approximately 4 hours until the temperature of the thawed AHF concentrate was 25.2° C.

It is important to note that all steps up to the optional freeze step were carried out at room temperature.

A forty-fold concentrated copper phenanthroline (CuPH) buffer was prepared by mixing 10 ml 0.1M histidine, 8 ml of 0.01M copper sulfate pentahydrate and 8 ml of 0.5M 1,10 phenanthroline. The final volume was adjusted to 200 ml. with WFI. A volume of 87.5 ml of the CuPH buffer was added to 3500 ml of the AHF concentrate in a sterilized, enclosed reactor. The enclosed CuPH reactor was constructed to rotate end to end to wet all internal surfaces. Oxygenation was delivered by diffusion through 25 feet of silastic medical grade tubing wound around a holder inside the reactor. During the reaction, medical grade oxygen at 2.5 psi was delivered to the reactor, which rotated at a rate of 3 rpm.

The CuPH reaction was started by the addition of 35 ml of 0.2M L-cysteine hydrochloride monohydrate as described in the above referenced U.S. Pat. No. 4,534,972. As described in this patent, a second addition of 17.5 ml of 0.2M L-cysteine hydrochloride was injected after the first addition was exhausted. The addition was also oxidized. Before emptying and rinsing the reactor, the reactor was transferred to a virus free room, and the outside of the reactor disinfected with sodium hypochloride. The CuPH reaction mixture was warmed to not more than 37° C. and prefiltered. The prefiltering step is not required but is utilized to preserve the lifetime of the gel filtration column. Four Pharmacia KS 370/15 stack sections were connected in series and run from bottom to top, using a MasterFlex pump. The prefiltered AHF was pumped onto the Pharmacia stack column packed with BioGel A-5M (100–200 mesh) at 8.4 l/hr, the loading range being 6–12 l/hr.

The AHF recovered from the CuPH reactor was 90% of the AHF in the AHF concentrate, the average being 88.3% with a range of 80.7–93.5%. In open CuPH reactors, such as in stirred beakers, an average recovery of 93.7% with a range of 88–98.7% was attained. These are very high yields compared to more conventional wet heat viral inactivation steps where approximately 25% loss of AHF activity is evidenced through pasteurization, diafiltration and ultrafiltration. Further, the mild processing steps also minimize the likelihood of deleterious effects on proteins.

The stack column was equilibrated with a buffer containing 0.15M NaCl, 0.001M $CaCl_2$, pH 7.16 at 22° C. Ranges for the buffer being not more than 0.2M NaCl, not more than 0.003M $CaCl_2$, pH 6.8–7.8, and temperature 16°–26° C. After the total of 3.9 Kg of the CuPH treated AHF had been pumped into the column, the same buffer used to equilibrate the column was used as an elution buffer. The elution buffer was pumped into the column at a flow rate of 9.0 l/hr, the range being 6–12 l/hr. Alternative buffers can be used, for example, 0.05M Trizma base, 0.15M NaCl, 0.001M $CaCl_2$, pH 7.4 or 0.02M L-histidine, 0.15M NaCl, 0.001M $CaCl_2$, pH 7.2. Since the elution buffer is present in the final container, it should be non-toxic and the ionic strength should not be so high that it dissociates the AHF from the von Willebrand factor.

The prefiltered CuPH treated AHF, 3.9 Kg, was gel filtered using 64 l of Bio-Rad's Biogel A5M (100–200 mesh) column equilibrated with the above described elution buffer, with application of 6.1% of the gel volume, the preferable range being 5–8.0% of the gel volume for efficient separation and yield. More gel volume would result in less potency in the AHF pool, less gel volume would lower the yield. The time between applying the AHF to the column until the beginning of the collection of the AHF pool was 2.35 hours. The collection of AHF pool was begun when the UV monitor indicated that $A_{280}$ was eluting. The void volume (Vo) was 20.03 Kg.

The AHF pool was collected until direct $A_{280}$ spectrophotometic reading indicated that an $A_{280}$ of 2.0 was obtained. A weight of 14.8 Kg of AHF pool was collected. Gel filtration is an effective means of removing the copper phenanthroline reactants, as evidenced by the fact that once the AHF pool is eluted, the pink CuPH reactants are still less than one-half way through the column. Furthermore, large proteins such as fibrinogen, and fibronectin are also separated out by gel filtration.

A series of experiments were conducted to confirm that CuPH reactants were removed and to evaluate residual levels of phenanthroline (PH) using radio-labelled $^{14}C$. $^{14}C$-PH was prepared and used to monitor the removal of the compound during various process steps. These results indicated that gel filtration is an effective procedure for removal of free PH from AHF and other proteins. Further studies showed that the association of pH with protein was decreased approximately 4 to 5 fold when the reaction was run in the presence of ammonium formate, histidine and mannitol. These compounds were added to the process to minimize the presence of small residual amounts of PH associated with the protein.

The recovered AHF pool had a pH of 6.85, an $A_{280}$ of 1.21, weight of 14.8 Kg and potency of 56.6 u/ml. This yields a specific activity of 56.6/1.21=46.8 units-/$A_{280}$ unit and a purification of 46.8/13 (for AHF concentrate)=3.6 fold. The yield through the column was 75.5%, with an average yield of 79.5% and a range of 70.1–89.9 from previous runs. Due to the high potency of the AHF pool (56.6 u/ml), no ultrafiltration was performed. In fact, the AHF pool had to be diluted with column buffer down to approximately 35 u/ml for further processing. However, if a higher final container concentration is desired, the AHF pool can be easily ultrafiltered to 100 to 300 u/ml, as shown in Examples 8 and 9.

Although this particular run of the AHF pool was not frozen, previous AHF pools from the gel filtration column have been frozen and stored at −70°, as a hold step until bulked and freeze dried.

Normal serum albumin was added such that the calculated final container potency would be approximately 25 u/ml. 492 ml of 25% albumin was added to aid in final container reconstitution. This amount of albumin corresponds to 5 mg albumin per ml of AHF solution, with a range of 1–10 mg albumin, more preferably 3–5 mg albumin/ml of AHF. In addition to albumin, the final container can contain stabilizing agents such as 0.2M glycine and 0.001M CaCl or 0.15M NaCl and 0.001M $CaCl_2$.

The human serum albumin (HSA) pool was sterile filtered using a 10 inch Duofine, a 12 inch CWSS and as a sterile filter, a 10 inch Millipore TP. The sterile filters were rinsed with fresh column buffer to a target bulk weight of 24.6 Kg. The AHF recovery through the sterile filtration was 91.5%, with an average of 85%, and a range of 78–92.6%. The $A_{280}$ of the sterile filtered AHF was 5.15.

The sterile AHF - HSA solution was mixed in a sterile bulk container and aseptically filled in 50 cc bottles, 20 ml in each bottle, and placed in a production freeze dryer and lyophilized. The yield across freeze drying was 89.8% with an average of 89.4% and a range of 78–111%.

The final containers were subjected to extensive analysis for quality control, and demonstrated a stable, pyrogen-free, sterile, safe preparation with very low levels of IgG, IgM, IgA, fibrinogen and fibronectin.

The concentration of the final container was 610 AHF units/20 ml, with a specific activity of 5.7 AHF units/mg protein and very low levels of copper and phenanthroline were detected.

EXAMPLE 2

Samples from the same lot of low specific activity, ultrafiltered AHF final container concentrate were gel filtered over various gel filtration (GF) columns and compared for their efficiency in separating AHF from the remainder of the other contaminants. The various gel filtration resins were poured into 2.6×25 cm columns and 10 ml of the concentrate applied and gel filtered. The results are shown in Table 1. Pool 1 represents the AHF pool collected by following $A_{280}$ from rise to 2.0, as described above. The Pool 2 represents all the rest of the $A_{280}$ eluted from the particular gel filtration column. The total recovery represents the sum of the yields in Pool 1 and 2.

From the table it can be seen that Pharmacia Cl-4B, Bio-Gel A-15M, and LKB Ultrogel A4 also give results that are similar to those obtained with Bio-Rad's BioGel A5M. In separate experiments it was found that the 100–200 mesh Bio-Gel A5M resin was optimal compared to the other two meshes. Mesh refers to U.S. Standard Wet Mesh Designation (hydrated).

These gels are selected to have fractionation ranges which enable the AHF/von Willebrand complex to be separated from the majority of other impurities, such as fibrinogen, fibronectin, etc.

Some of the gels shown in Table 1 resulted in less than 50% yield of AHF, presumably because of poor fractionation ranges. All would serve to remove chemical reactants from the described vital inactivation steps, since such reactants have an MW less than 300 d.

The Pharmacia gels are all cross-linked beaded agarose. The Bio-Gel resins are all agarose-based gels. LKB Ultrogel A4R has 4% agarose beads. The Fractogels are hydophilic semi-rigid spherical gels prepared from vinyl polymers. The CPG series refers to controlled pore glass beads.

TABLE 1

| | No. of runs | Comparative gel filtration resins | | | Pool 2 Yield | Total Recovery VIII:C |
|---|---|---|---|---|---|---|
| | | Pool 1 | | | | |
| | | Yield | Sp. Act. | Purification | | |
| Pharmacia Cl 2B | 6 | 27% | 7.6 | 13× | 61% | 88% |
| Pharmacia Cl 4B | 7 | 54% | 12.8 | 21.4× | 37.5% | 91% |
| Pharmacia Cl 6B | 3 | 37% | 6.8 | 11.3× | 55% | 82% |
| BioGel A-5M (50-100 Mesh) | — | 61% | 11.2 | 17.2× | 51% | 99% |
| BioGel A-5M (100-200 Mesh) | — | 67% | 15.7 | 24.1× | 41% | 103% |
| BioGel A-5M (200-400 Mesh) | 5 | 66% | 14 | 21.8× | 34% | 99% |
| BioGel A-15M (200-400 Mesh) | 6 | 51.2% | 12.6 | 21.2× | 32% | 83.1% |
| BioGel A-50M (100-200 Mesh) | 6 | 44% | 10 | 17× | 51% | 96% |
| BioGel A-150M | 5 | 22% | 6.1 | 11× | 74% | 96% |
| LKB Ultrogel A4 | 5 | 64% | 13 | 21× | 41% | 100% |
| CPG - 75 | 3 | 14% | .57 | — | 77% | 91% |
| CPG - 500 | 6 | 55% | 4.9 | 4.9× | 31% | 86% |
| CPG - 1000 | 5 | 34% | 15 | 26× | 60% | 93% |
| Fractogel TSK-65 | 6 | 30% | 5.5 | 5.4× | 53% | 83% |
| Fractogel TSK-75 | 7 | 30.4% | 14 | 10× | 52% | 82% |

Example 3

To demonstrate that copper phenanthroline provides a useful approach to reduce the risk of viral transmission from therapeutic biological products, solubilized AHF concentrates were spiked with viruses from different taxonomic groups and treated with CuPH.

An enclosed reactor was designed, constructed and tested for its ability to inactivate model viruses. Volumes of 3.5 to 4.0 L of AHF concentrate were used to validate the reactor. The temperature was from 23° to 27° C. Oxygen to drive the CuPH reaction was delivered by diffusion at 2.5 psig through 25 ft. of silastic tubing wound in a holder inside the reactor (see Example 1). A tumbler rate of 3 RPM was chosen. Sindbis, Vesicular Stomatitis virus (VSV) and Visna viruses were added to the reactor prior to initiation of the CuPH reaction. The following table summarizes the full scale production concentrates evaluation of virus inactivation by CuPH.

TABLE II

| | CuPh Reactor Virus Challenges | | |
|---|---|---|---|
| | Control-0 Time | End of 1st CuPH Reaction | End of 2nd CuPH Reaction |
| $\log_{10}$ VSV[a] | 7.2 | 2.6 | 0.7 |
| $\log_{10}$ SINDBIS[b] | 5.0 | ≦1.5 | ≦1.5 |
| $\log_{10}$ VISNA[b] | 5.0 | 3.5 | ≦1.5 |

TABLE II-continued

| | CuPh Reactor Virus Challenges | | |
|---|---|---|---|
| | Control-0 Time | End of 1st CuPH Reaction | End of 2nd CuPH Reaction |
| log$_{10}$ VISNA[b] | 5.0 | 2.75 | ≦1.5 |

[a]refers to P.F.U./ml or Plaque Forming Units/ml of VSV
[b]refers to T.C.I.D.$_{50}$/ml or Tissue Culture Infectious Dose - 50%/ml As can be seen from the table, the model viruses were all inactivated to a great degree. No detectable virus could be found following the CuPH reaction in the reactor when SINDBIS or 2 runs of VISNA virus were added. Due to the toxicity of the AHF GF - CuPH reactants, undiluted samples could not be titered. The final titer of ≦1.5 logs of virus represents no detectable virus in any of the samples tested at a dilution of 1:10. In the VSV challenge one plaque was observed on one of the duplicate assay plates. However, 6.5 logs of VSV were inactivated in this reactor run. These results verify that the extent of virus inactivation using full scale production conditions was comparable with those virus challenges performed in small scale stirred vessels.

Example 4

In collaboration with U. C. Davis, virus challenges with Human Immunodeficiency Virus (HIV), VSV and Visna virus were performed in small scale stirred cells. The AHF solutions tested included 10% normal HIV negative serum and AHF concentrates as described in Example 3. Virus was added to the stirred serum or AHF concentrate and the CuPH reaction initiated by the addition of 0.002M L-Cysteine. A second volume of cysteine was added to each sample after 30 minutes. (See Table II). The CuPH reaction inactivated HIV in 10% serum, as well as in the AHF concentrate. As before for Example 3, we could not titer the viruses (see Table III) undiluted, due to toxicity of the CuPH reagents themselves. Therefore, the end titer is expressed as ≦1.0 log of HIV. There was no detectable HIV or Visna in AHF concentration at a dilution of 1:10; 5.25 logs of VSV were inactivated during the CuPH reaction in the AHF concentrate.

TABLE III

| | Virus Challanges | | | | | |
|---|---|---|---|---|---|---|
| | VSV spike | | Visna spike | | HIV spike | |
| Time | serum | AHF | serum | AHF | serum | AHF |
| 0 | 7.25* | 7.50 | 4.00 | 5.50 | 4.5 | 6.15 |
| first 30' | 2.00 | 4.50 | ≦1.50 | ≦1.50 | ≦1.0 | ≦1.2 |
| second 30' | ≦1.50 | 2.25 | ≦1.50 | ≦1.50 | ≦1.0 | ≦1.0 |

*Virus titer, log$_{10}$ TCID$_{50}$/ml

Example 5

In addition to the usual location of the chemical treatment step to inactivate contaminating viruses, two other steps in the reported process were also treated with CuPH. The two sites that were examined were 1) dissolved cryosolution and 2) PEG effluent. After the CuPH treatment of the respective site, normal processing was continued including the BioGel A5M column. The starting volume was 1260 ml of dissolved cryo (1 part cryo to 3 parts WFI). To 400 ml of the dissolved cryo, pH 7.0 was added 10 ml of a forty-fold concentrated CuPH buffer (see Example 1) followed by the addition of 4 ml of 0.2M L-cysteine to start the CuPH reaction. A second volume of 0.2M L-cysteine was added 15 minutes after the first addition. The rest of the cryo solution was processed simultaneously (860 ml) until the PEG effluent when 400 ml of that solution was treated with CuPh. At the end of the gel filtration columns there were four samples: 1) Control no CuPh at all, 2) CuPH treated cryo, pH 7.0, 3) CuPH treated PEG effluent, 4) CuPH treated AHF concentrate (normal process). The results of this set of studies is summarized in Table IV. There is very little difference between any of the samples. The overall yields from dissolved cryo to the gel filtered AHF Pool 1 are very close (45.1% to 50.7%). These results indicate that the site of the virus inactivation treatment could be extended to include these locations. The only potential drawback would be that all subsequent steps following the CuPH treatment would have to be performed in a virus-free room to insure a safe environment.

TABLE IV

| Alternative Sites For CuPH Treatment | | | | |
|---|---|---|---|---|
| | Control No CuPH | CupH Cryo | CuPH PEG EFF. | CuPH AHF Conc. |
| AHF Yield - CuPH Step | — | 81.3% | 102% | 90.9% |
| AHF Yield - Cryo to PEG EFF | 91.9% | 83.5% | 91.9% | 91.9% |
| AHF Yield - Cryo to AHF Conc. | 75.8% | 63.9% | 67.3% | 75.8% |
| AHF Yield - PEG EFF to AHF Conc. | 82.5% | 76.5% | 73.0% | 82.5% |
| AHF Yield - AHF Conc. to Pool 1 | 63.9% | 70.5% | 71.9% | 66.9% |
| Sp. Act. - Pool 1 | 35.5 | 31.8 | 31.3 | 37.2 |
| AHF Yield-Cryo to Pool 1 | 48.4% | 45.1% | 48.4% | 50.7% |

Example 6

Another vital inactivation process which may be utilized in the process of the present invention is described in U.S. Pat. No. 4,540,573. Briefly, this process involves contacting AHF concentrates with tri-N-butyl phosphate (TNBP) plus a detergent such as Tween 80, Triton X-100 or cholate.

A sample of a typical AHF concentrate (just prior to gel filtration) was treated with various TNBP/detergents for 6 hours at 30° along with an AHF control not containing the TNBP/detergent. The TNBP levels added to the concentrate and results are shown in Table V below.

TABLE V

| Effect of TNBP/Detergent on AHF Recovery | | | |
|---|---|---|---|
| Sample | Time at 30° | AHF (u/ml) | % Loss |
| Control AHF | 0 | 186.8 | — |
| Control AHF | 6 | 186.7 | 0 |
| 0.3% TNBP/ 0.2% Cholate | 6 | 141.4 | 24.3 |
| 0.3% TNBP/ 1% Tween 80 | 6 | 169.7 | 9.1 |
| 0.3% TNBP/ 0.2% Triton-X-100 | 6 | 167.5 | 10 |

The above Table V demonstrates that a TNBP/detergent treatment at the same step in the process as the previously described CuPH step does not result in large losses of AHF in the present process. Under the process conditions shown, a yield loss of 10% or less may be obtained.

Example 7

This Example demonstrates that a gel filtration step may be employed according to the present process subsequent to the above-described TNBP/detergent treatment to remove the added chemicals.

A sample of the same AHF concentrate used in Example 6 was treated with 0.3% TNBP/1% Tween 80 for 6 hours at 30°. Exactly 8.75 ml of the treated AHF concentrate was then gel filtered over a 125 ml Biogel A5M column, prepared as described in Example 2. The resulting AHF Pool 1 and the Pool 2, as described in connection with Table 1, were checked for the presence of TNBP, Tween, and AHF activity. The results are shown below in Table VI.

TABLE VI

Gel Filtration of TNBP/Tween 80 Treated AHF

| Sample | AHF (u/ml) | Sp. Act. | Step Yield (%) | TNBP (ppm) | Tween 80 (ppm) |
|---|---|---|---|---|---|
| Control AHF | 192.6 | 5.8 | — | — | — |
| TNBP/Tween AHF | 180.8 | 5.3 | 93.9 | 3200 | 5878 |
| Pool 1 | 57.4 | 41.6 | 87.1 | ≦0.8 | ≦0 |
| Pool 2 | 1.8 | 0.34 | 5.6 | 120 | 861 |

In this experiment, 93.9% of the initial AHF remained following TNBP/Tween 80 treatment and the AHF Pool (Pool 1) was found to contain 87.1% of the applied AHF, with no detectable TNBP or Tween. The Pool 1 specific activity of 41.6 was very similar to that obtained for this concentrate as used in Example 1, in which the concentrate was gel filtered after previously being subjected to a CuPH treatment.

An identical experiment to that detailed in Table VI was performed using 0.3% TNBP/1% Triton X-100, and similar results were obtained.

Example 8

The AHF pool from a production column run was ultrafiltered (UF) using Amicon hollow fiber cartridges (10 sq. ft.). The AHF pool (16.2 Kg) was ultrafiltered in 1 hour to a weight of 4.8 Kg. The following table summarizes the pertinent data for the ultrafiltration step.

TABLE VII

Ultrafiltration of Gel Filtered AHF

| Step | Weight (Kg) | $A_{280}$ | AHF (u/ml) | Specific Activity | Total AHF (units) | Yield (%) |
|---|---|---|---|---|---|---|
| AHF Pool (1) | 16.2 | 0.93 | 57.1 | 61.4 | 925,020 | — |
| U.F. Pool (1) | 4.8 | 2.95 | 182.4 | 61.8 | 875,520 | 94.7 |

The AHF pool was ultrafiltered very easily with no loss in purity and very little loss in yield (approximately 5%). The AHF potency was concentrated to >180 units per ml. In separate experiments it has been possible to easily ultrafilter AHF Pool (1) to greater than 300 units of AHF per ml. At this high potency, a very low volume of reconstituted final container will enable the hemophiliac to receive a large quantity of AHF quickly. The final container potency will depend upon the extent of ultrafiltration. Expected range of final container potencies is between 50 to 300 units per ml of AHF.

Example 9

The ultrafiltered AHF Pool (1) from Example 8 was diluted with column buffer and normal serum albumin was added such that the calculated final container potency would be approximately 100 u/ml. After sterile filtration (as in Example 1) and lyophilization, the final container AHF concentrate was assayed, and some of these results are tabulated in Table VIII.

TABLE VIII

Final Container Test Results on TNBP/Tween AHF

| Test | Results |
|---|---|
| AHF Potency | 104 u/ml |
| von Willebrand Factor (vWF) | 95 u/ml |
| Specific Activity | 16.8 units/mg protein |
| TNBP | ≦0.8 ppm |
| Tween 80 | ≦0 ppm |
| Rabbit Pyrogen | pass |
| Sterility | pass |
| Safety | pass |
| Fibronectin | 0.39 mg/ml |
| Fibrinogen | <0.6 mg/ml |
| IgG | <0.015 mg/ml |

As can be seen in the table, an AHF concentrate can be prepared at 4 times the usual 25 u/ml dose and not affect the final container properties. There was no problem in sterile filtering this AHF pool. The rabbit pyrogen test was performed by injecting 100 units AHF per Kg of rabbit and the total temperature rise in three rabbits was only 0.3° C. The calculated ratio of von Willebrand to AHF Factor of 0.91 implies an almost ideal plasma ratio of 1.0 in the final container. Anywhere from 0.5 to 2.0 can be obtained with the present process, 0.75 to 2.0 being preferred. Concentrations can be highly controlled in the present process, although at least 25 u/ml of vWF is regarded as a minimum for the present process.

Non-detectable TNBP and Tween 80 were found in this final container AHF concentrate. The production scale run verifies the small scale results already documented in Example 7 and Table VI.

TABLE IX

| | Lot 1 | Lot 2 | Lot 3 | Lot 4 | Lot 5 | Lot 6 |
|---|---|---|---|---|---|---|
| Fill size, ml/vial | 10 | 10 | 40 | 20 | 20 | 5 |
| AHF, u/ml | 36 | 32 | 27.5 | 24.7 | 30.3 | 104 |
| vWF, u/ml | 52 | 32 | 40 | 41 | 31 | 95 |
| Protein, mg/ml | 5.4 | 5.3 | 5.2 | 5.2 | 5.3 | 6.2 |
| Pool 1 specific activity | 55 | 47.2 | 47.2 | 44.3 | 46.8 | 61.4 |
| Specific activity | 6.7 | 6 | 5.3 | 4.8 | 5.7 | 16.8 |
| Ratio VIII RcoF/VIII:C | 1.4 | 1 | 1.5 | 1.7 | 1 | 0.91 |
| Non-protein Nitrogen | 0.37 | 0.38 | 0.37 | 0.01 | 0.03 | 0.5 |
| Units AHF/mg Fibrinogen | >60 | >53.3 | >45.8 | >41.2 | >50.4 | >173 |
| Fibronectin, mg/ml | 0.8 | 0.11 | 0.05 | 0.03 | 0.1 | 0.39 |
| Fibrinogen, mg/ml | <0.6 | <0.6 | <0.6 | <0.6 | <0.6 | <0.6 |
| IgA, mg/ml | <0.05 | <0.05 | <0.05 | <0.05 | <0.05 | <0.05 |
| IgG, mg/ml | <0.015 | <0.015 | <0.015 | <0.015 | <0.015 | <0.015 |

Table IX shows additional assay results from various lots. The ratio of vWF to AHF is shown as Ratio VIII RcoF/VIII:C.

It should also be noted that amino acids are not added to stabilize the present composition. Therefore, the non-protein nitrogen (i.e., amino acids) will be less than 1%.

Thus there has been described a process for the preparation of AHF comprising a sequence of precipitation, solubilization, gel filtration and vital inactivation steps. Notwithstanding that reference has been made to specific preferred embodiments, it will understood that the present invention is not be construed as limited to such, but rather to the lawful scope of the appended claims.

What is claimed is:

1. An antihemophilic factor concentrate, free of non-human protein, substantially free of viral infectious agents, having 1–10 mg human serum albumin per ml of reconstituted solution, having a ratio of von Willebrand activity units/ml to the antihemophilic factor clotting activity units/ml of 0.75 to 2.00, and having a specific activity of at least 40 units of antihemophilic factor clotting activity per mg protein, excluding said human serum albumin, the concentrate being free of a viral inactivation compound.

2. The composition of claim 1 comprising not more than 1% non-protein nitrogen.

3. The composition of claim 1 having at least 41.2 units of antihemophilic factor clotting activity per mg of fibrinogen.

* * * * *